(12) United States Patent
Suzuki

(10) Patent No.: US 6,387,083 B1
(45) Date of Patent: *May 14, 2002

(54) PULL-ON DISPOSABLE DIAPER

(75) Inventor: Seiji Suzuki, Kagawa-ken (JP)

(73) Assignee: Uni-Charm Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/338,067

(22) Filed: Jun. 23, 1999

(30) Foreign Application Priority Data

Jun. 30, 1998 (JP) .......................... 10-185042

(51) Int. Cl.⁷ ............................... A61F 13/15
(52) U.S. Cl. ..................... 604/385.01; 604/385.23; 604/385.31
(58) Field of Search ............... 604/385.01, 385.23, 604/385.24, 385.25, 385.26, 385.31

(56) References Cited

U.S. PATENT DOCUMENTS

| | | | | |
|---|---|---|---|---|
| 4,205,679 A | | 6/1980 | Repke et al. | |
| 4,743,241 A | * | 5/1988 | Igaue et al. | |
| 5,163,932 A | * | 11/1992 | Nomura et al. | |
| 5,624,420 A | * | 4/1997 | Bridges et al. | 604/365 |
| 5,626,574 A | * | 5/1997 | Sasaki et al. | |
| 5,769,838 A | * | 6/1998 | Buell et al. | |
| 5,855,574 A | * | 1/1999 | Kling et al. | 604/392 |
| 6,120,487 A | * | 9/2000 | Ashton | |

FOREIGN PATENT DOCUMENTS

| | | |
|---|---|---|
| EP | 0 597 331 A1 | 5/1994 |
| WO | WO 95/00096 | 1/1995 |

* cited by examiner

*Primary Examiner*—Dennis Ruhl
(74) *Attorney, Agent, or Firm*—Baker & Daniels

(57) ABSTRACT

A pull-on disposable diaper has front and rear waist regions placed upon each other along their respective side edges and bonded together at outer bonding zone intermittently arranged along these side edges. A plurality of sheet materials forming the respective side edges of the front and rear waist regions are bonded together along an inner bonding zones vertically extending inside each of the outer bonding zone. The inner bonding zone prevents transversely opposite side edges of the diaper from being torn in a circumferential direction thereof, when the transversely opposite side edges of the diaper are torn off vertically of the diaper.

4 Claims, 2 Drawing Sheets

PULL-ON DISPOSABLE DIAPER

BACKGROUND OF THE INVENTION

This invention relates to a pull-on disposable diaper for absorption and containment of body wastes.

Japanese Patent Application Disclosure Gazette (Kokai) No. Hei5-15551 discloses a pull-on disposable diaper in which front and rear waist regions comprising a topsheet and a backsheet containing heat-sealable materials are placed upon each other along their respective side edges and heat-sealed together at heat-sealing spots intermittently arranged on the side edges vertically of the diaper. A wearer of such diaper can be stripped thereof by tearing the diaper from top to bottom along the respective arrays of the heat-sealing spots so that the front and rear waist regions may be separated from each other forth and back. By stripping the wearer of the diaper in this manner, the wearer's legs can be protected from being soiled with body wastes.

With the pull-on disposable diaper according to the above-mentioned prior art, if the topsheet and/or the backsheet are fiber-oriented transversely of the diaper, the lines along which the diaper should be torn are apt to turn aside following the fiber orientation in the course of tearing the diaper vertically thereof. Such a tendency often makes it difficult to tear off the diaper in an orderly manner.

SUMMARY OF THE INVENTION

In view of the problem as has been described above, it is an object of the present invention to provide a pull-on disposable diaper having front and rear waist regions placed upon and bonded to each other along their respective side edges improved so that the diaper may be torn off in a relatively easy manner in the vertical direction.

According to the present invention, there is provided a pull-on disposable diaper having a front waist region and a rear waist region, the diaper comprising a liquid-pervious topsheet, a liquid-impervious backsheet and a liquid-absorbent core disposed between the topsheet and the backsheet, each of transversely opposed side edges of the front and rear waist regions being placed upon each other and bonded together at an outer bonding zone intermittently arranged on each of the side edges in a vertical direction of the diaper.

Each of the side edges of the front and rear waist regions bonded together comprises a plurality of sheet materials placed one upon another, the plurality of sheet materials being bonded together along an inner bonding line extending in parallel to the outer bonding line at each of the front and rear waist regions, with said inner bonding line being spaced inwardly from the outer bonding line by 3~20 mm.

According to one preferred embodiment of the present invention, at least one of the plurality of sheet materials contains thermoplastic synthetic resin, the inner bonding line is formed by heat-sealing the thermoplastic synthetic resin.

According to another preferred embodiment of the present invention, the plurality of sheet materials placed one upon another along each of the side edges comprise the topsheet and the backsheet.

According to still another preferred embodiment of the present invention, one of the topsheet and the backsheet includes a nonwoven fabric fiber-oriented transversely of the diaper.

According to further another preferred embodiment of the present invention, the backsheet is a laminate sheet comprising a thermoplastic synthetic resin film as an inner layer and a nonwoven fabric of thermoplastic synthetic resin as an outer layer.

DETAILED DESCRIPTION OF THE PREFERRED EMBODIMENT

Details of a pull-on disposable diaper according to the present invention will be more fully understood from the description given hereunder with reference to the accompanying drawings.

Figure 1:
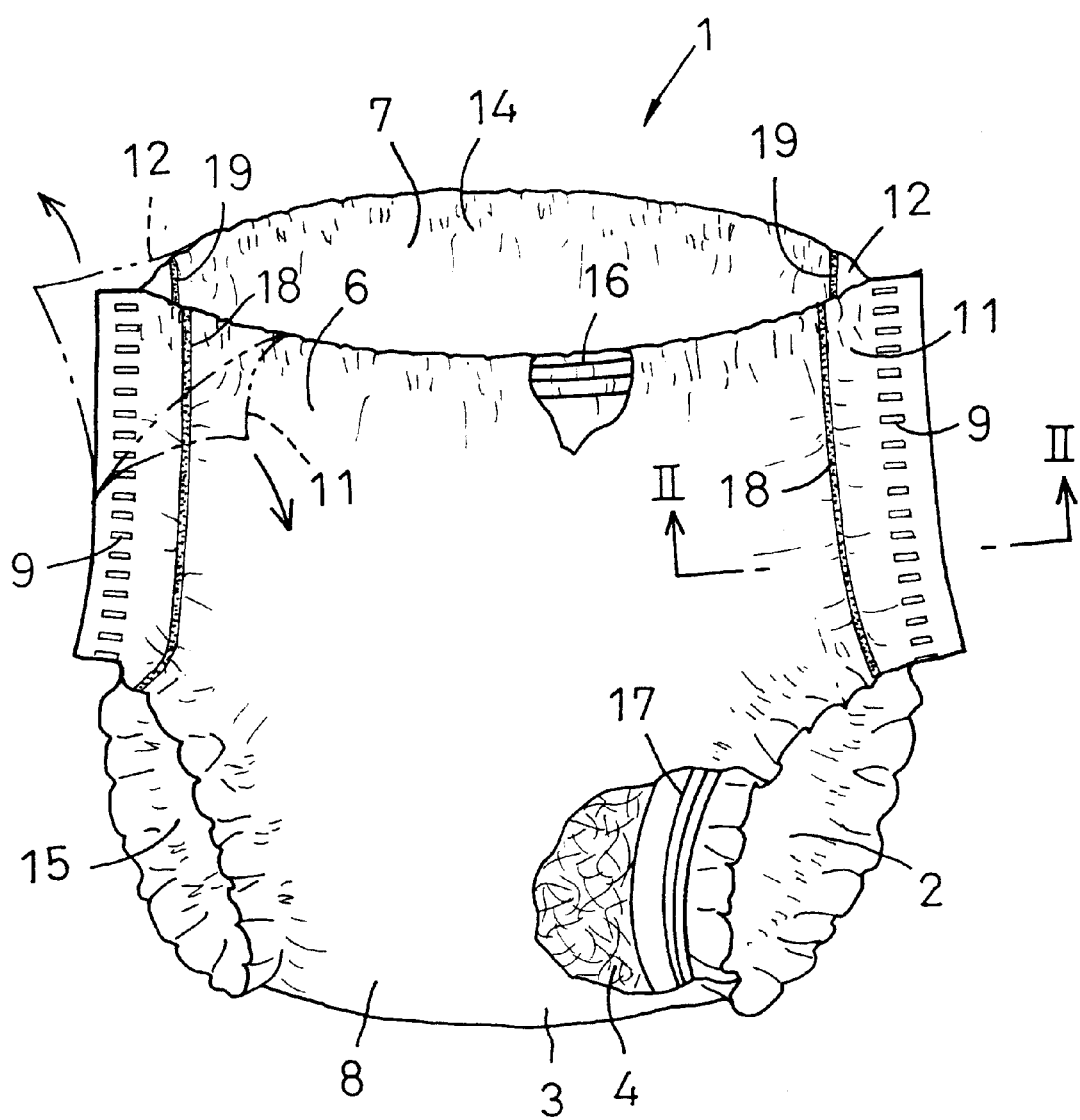
FIG. 1 is a perspective view showing a pull-on disposable diaper according to one embodiment of the present invention as partially broken away.

A pull-on disposable diaper 1 shown by FIG. 1 in a perspective view as partially broken away comprises a liquid-pervious topsheet 2, a liquid-impervious backsheet 3 and a liquid-absorbent core 4 disposed between these two sheets 2, 3. The topsheet 2 and the backsheet 3 are bonded to each other along their portions extending outward beyond a peripheral edge of the absorbent core 4. Configurationally, the diaper 1 is composed of a front waist region 6, a rear waist region 7 and a crotch region 8 extending between these two waist regions 6, 7. The front and rear waist regions 6, 7 are placed upon each other along their respectively opposite side edges 11, 12 and bonded together at vertically intermittent bonding spots 9 arranged along the respective side edges 11, 12. The diaper 1 further has a waist-opening 14 and a pair of leg-openings 15, these openings 14, 15 being provided along their peripheral edges with elastic members 16, 17 secured under appropriate tension, respectively. The elastic member 16 is adapted to surround a wearer's torso and the elastic members 17 are adapted to surround the wearer's legs. The elastic members 16, 17 are disposed between the topsheet 2 and the backsheet 3 and are bonded to an inner surface of at least one of these sheets 2, 3. The topsheet 2 and the backsheet 3 are bonded to each other not only at the bonding spots 9 but also along bonding lines 18, 19 respectively extending from edges of the waist-opening 14 to edges of the leg-openings 15 in parallel to the respective side edges 11, 12 of the front and rear waist regions 6, 7 inside each of the arrays of bonding spots 9.

In such diaper 1, a certain amount of thermoplastic synthetic resin is contained in the topsheet and/or the backsheet 3. For example, the topsheet 2 may be made of a apertured film of thermoplastic synthetic resin or a non-woven fabric of thermoplastic synthetic resin and the backsheet 3 may be made of a thermoplastic synthetic resin film or of a laminate sheet comprising the film as an inner layer and a nonwoven fabric of thermoplastic synthetic fiber as an outer layer. These topsheet 2 and the backsheet 3 are bonded to each other along the arrays of bonding spots 9 and the bonding lines 18, 19 by means of suitable adhesive agent or the heat-sealed amount of the thermoplastic synthetic resin making a part of the topsheet 2 and the backsheet 3.

Figure 2:
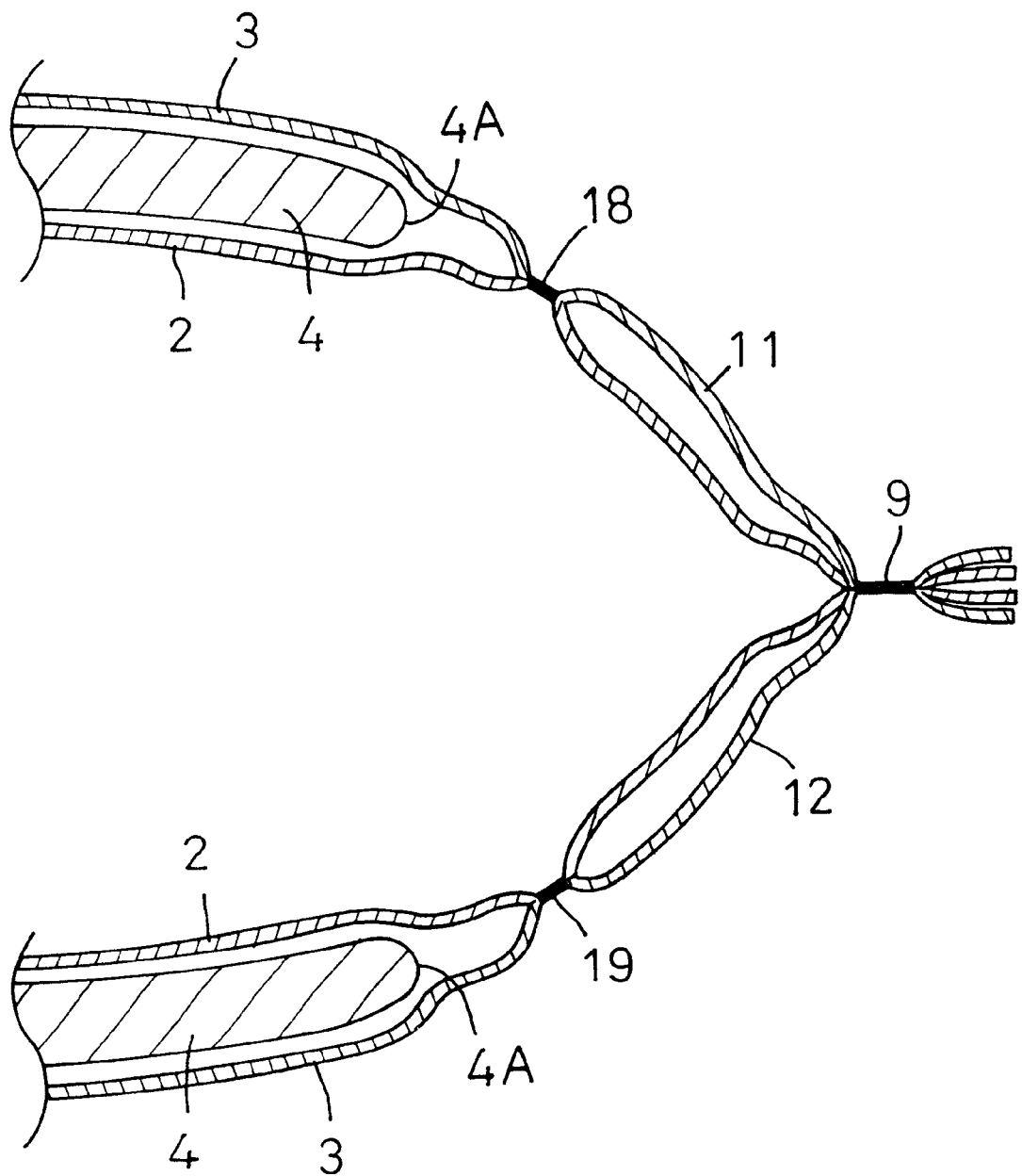
FIG. 2 is a sectional view taken along a line II—II in FIG. 1.

FIG. 2 is a sectional view taken along a line II—II in FIG. 1. Portions of the topsheet 2 and the backsheet 3 forming the respective side edges 11, 12 of the front and rear waist regions 6, 7 are placed upon and bonded to each other along the arrays of bonding spots 9. In addition, the topsheet 2 and the backsheet 3 are bonded to each other also along the bonding lines 18 and 19 in the front and rear waist regions 6, 7, respectively. The bonding lines 18, 19 lie between the arrays of bonding spots 9 and respective side edges 4A of the absorbent core 4, preferably inward spaced from the respective arrays of bonding spots 9 by 3~20 mm.

When it has been perceived that feces has been discharged on the diaper 1 of such an arrangement worn by a baby, the baby may be stripped of his or her diaper 1 by tearing off the front and rear waist regions 6, 7 along the arrays of bonding spots 9 of the diaper 1 so that these two waist regions 6, 7 are separated from each other forth and back. It should be minded here that, if the nonwoven fabric or the synthetic resin film used as the stock material for the topsheet 2 and/or the backsheet 3 are oriented circumferentially of the diaper 1, the tear will be apt to turn aside in the circumferential direction on the way of tearing the diaper 1 in the vertical direction. Such a tendency sometimes makes it difficult to separate the front and rear waist regions 6, 7 from each other in an orderly manner. However, in the case of the diaper 1 according to the present invention, even when the respective side edges 11, 12 of the front and rear waist regions 6, 7 being torn off begin to be torn in the circumferential direction, the respective tears can not further run across the bonding lines 18, 19 and run again downward without running in the circumferential direction.

Each of the bonding lines 18, 19 is preferably dimensioned to be 1~7 mm wide, more preferably to be 1~5 mm wide and preferably depressed in the direction of sheet thickness so that a touch of the diaper should not be deteriorated due to the presence of these bonding lines 18, 19. While the bonding lines 18, 19 are shown to extend from the edge of the waist-opening 14 to the edges of the respective leg-openings 15, the alternative embodiments are possible in which, adjacent the elastic members 16 for the waist-opening 14 as well as the elastic members 17 for the leg-openings 15, the topsheet 2 and the backsheet 3 are bonded together without containing these members 16, 17 therebetween. An arrangement is also possible in which the bonding lines 18, 19 lie in an extent defined below the elastic member 16 associated with the waist-opening 14 and above the elastic members 17 associated with the respective leg-openings 15. While the respective side edges 11, 12 of the front and rear waist regions 6, 7 are shown to be formed by the topsheet 2 and the backsheet 3, an alternative arrangement is also possible in which a third sheet is disposed between the topsheet 2 and the backsheet 3 or extension sheet material such as a sheet having a breathability or a heat durability higher than those of the topsheet 2 and the backsheet 3 is put to the topsheet 2 and the backsheet 3 so that such extension sheet may form the respective side edges 11, 12.

The pull-on disposable diaper according to the present invention is advantageously characterized in that a plurality of sheets forming the front and rear waist regions of the diaper are bonded together along the bonding lines extending vertically of the diaper inside the arrays of bonding spots along which the respective side edges of the front and rear waist regions placed upon and bonded to each other. This unique arrangement is effective to avoid any apprehension that, when the side edges of the diaper are torn off, the tears might turn aside in the circumferential direction and inwardly run across the respective bonding lines.

What is claimed is:

1. A pull-on disposable diaper having a front waist region and a rear waist region, said diaper comprising:

a liquid-pervious topsheet;

a liquid-impervious backsheet;

a liquid-absorbent core disposed between said liquid-pervious topsheet and said liquid impervious backsheet; and transversely opposite side edges of each of said front and rear waist regions are respectively defined by portions of both said liquid-pervious topsheet and said liquid-impervious backsheet which extend outward from transversely opposite side edges of said liquid-absorbent core, said portions of said liquid-pervious topsheet and said liquid-impervious backsheet which extend outward from transversely opposite side edges of said liquid-absorbent core being placed upon each other and bonded together intermittently along outer bonding lines which extend on each of said side edges in a vertical direction, to define a waist-opening and a pair of leg-openings, said portions of said liquid-pervious topsheet and said liquid-impervious backsheet which extend outward from transversely opposite side edges of said liquid-absorbent core being continuously bonded together along inner bonding lines which extend parallel to said outer bonding lines at each of said front and rear regions, with said inner bonding lines being spaced apart inwardly from said outer bonding lines by about 3 to about 20 mm.

2. The diaper according to claim 1, wherein at least one of said liquid-pervious topsheet and said liquid-impervious comprises a thermoplastic synthetic resin and said inner bonding lines are formed by heat-sealing said thermoplastic synthetic resin.

3. The diaper according to claim 1, wherein at least one of said liquid-pervious topsheet and said liquid-impervious backsheet comprises a nonwoven fabric fiber oriented transversely of said diaper.

4. The diaper according to claim 1, wherein said liquid-impervious backsheet is a laminate sheet comprising a thermoplastic synthetic resin film as an inner layer and a nonwoven fabric of thermoplastic synthetic resin as an outer layer.

* * * * *